United States Patent
Naik

(10) Patent No.: US 11,810,658 B2
(45) Date of Patent: Nov. 7, 2023

(54) SYSTEM AND METHOD FOR TRACKING WELLNESS ACTIVITY USING A FITNESS TRACKING DEVICE

(71) Applicant: Visa International Service Association, San Francisco, CA (US)

(72) Inventor: Shweta Sitaram Naik, Redwood Shores, CA (US)

(73) Assignee: Visa International Service Association, San Francisco, CA (US)

(*) Notice: Subject to any disclaimer, the term of this patent is extended or adjusted under 35 U.S.C. 154(b) by 308 days.

(21) Appl. No.: 17/205,801

(22) Filed: Mar. 18, 2021

(65) Prior Publication Data

US 2021/0210191 A1 Jul. 8, 2021

Related U.S. Application Data

(63) Continuation of application No. 15/674,966, filed on Aug. 11, 2017, now Pat. No. 11,003,741.

(51) Int. Cl.
G16H 20/70 (2018.01)
G06Q 30/0238 (2023.01)

(52) U.S. Cl.
CPC ......... *G16H 20/70* (2018.01); *G06Q 30/0238* (2013.01)

(58) Field of Classification Search
None
See application file for complete search history.

(56) References Cited

U.S. PATENT DOCUMENTS

| | | |
|---|---|---|
| 2008/0096726 A1 | 4/2008 | Riley et al. |
| 2008/0147502 A1 | 6/2008 | Baker |
| 2010/0228561 A1* | 9/2010 | Boyce .............. G06Q 30/02 707/E17.107 |
| 2012/0041767 A1 | 2/2012 | Hoffman et al. |
| 2013/0196297 A1 | 8/2013 | Anwar |
| 2014/0297393 A1 | 10/2014 | Phillipps |
| 2015/0356701 A1 | 12/2015 | Gandy et al. |
| 2016/0092654 A1 | 3/2016 | Bryant |
| 2016/0371998 A1* | 12/2016 | Fazeel .............. G16H 20/30 |
| 2017/0039886 A1 | 2/2017 | Bitran et al. |
| 2017/0103677 A1 | 4/2017 | Bhattacharjee et al. |
| 2018/0053440 A1* | 2/2018 | Staveley .......... G09B 19/0092 |
| 2018/0075420 A1 | 3/2018 | Barnett et al. |
| 2018/0082041 A1 | 3/2018 | Bryant, II |
| 2018/0211274 A1 | 7/2018 | Gore et al. |
| 2018/0278691 A1 | 9/2018 | Vergara |
| 2019/0026364 A1* | 1/2019 | Sankovsky .......... G06Q 40/08 |

\* cited by examiner

*Primary Examiner* — Robert A Sorey
(74) *Attorney, Agent, or Firm* — THE WEBB LAW FIRM

(57) ABSTRACT

A method for tracking and incentivizing wellness activity using a fitness tracking device includes: receiving user wellness data collected over a time period from at least one fitness tracking device of a user, the user wellness data including at least one wellness metric corresponding to the user; analyzing user transaction data including transactions initiated by the user with a portable financial device over the time period; automatically determining a wellness award for the user based at least partially on the user wellness data and the user transaction data for the time period; and automatically initiating the wellness award for the user. A system for tracking and incentivizing a wellness activity using a fitness tracking device is also disclosed.

20 Claims, 9 Drawing Sheets

| Daily Step Count | % Back | Amount of Daily Purchases | Award Amount |
|---|---|---|---|
| 5,000 | 1.0% | $100 | $1.00 |
| 10,000 | 2.0% | $100 | $2.00 |
| 15,000 | 2.5% | $100 | $2.50 |
| 20,000 | 3.0% | $100 | $3.00 |
| 25,000 | 3.5% | $100 | $3.50 |
| 30,000 | 4.0% | $100 | $4.00 |

FIG. 3

| | User Wellness Goal | Date Entered | Status | % Back Assigned Upon Completion |
|---|---|---|---|---|
| 1 | Complete a 5k race in May | 04-10-2017 | Approved | 2.0% |
| 2 | Take 2,000 steps every day in May | 04-15-2017 | Rejected | — |
| 3 | Sleep 8+ hours every day this week | 04-23-2017 | Approved | 1.0% |
| 4 | Be active for at least 30 minutes each day this weekend | 04-27-2017 | Pending | |

| | Suggested Goal | % Back Assigned Upon Completion | Accept/Reject Goal? | |
|---|---|---|---|---|
| 1 | Take 10,000 steps today | 1.0% | ✓ | ✗ |
| 2 | Run 3 miles today | 1.5% | ✓ | ✗ |
| 3 | Consume fewer than 2,000 calories today | 1.0% | ✓ | ✗ |
| 4 | Take 10,000 steps every day in May | 3.0% | ✓ | ✗ |
| 5 | Complete 1 marathon in next 6 months | 4.0% | ✓ | ✗ |
| 6 | Sleep >7.5 hours every day in May | 2.5% | ✓ | ✗ |
| 7 | Purchase a gym membership in May | 1.5% | ✓ | ✗ |
| 8 | Spend $250 on organic food in May | 2.5% | ✓ | ✗ |
| 9 | Purchase fast food meal less than two times in May | 1.5% | ✓ | ✗ |

SYSTEM AND METHOD FOR TRACKING WELLNESS ACTIVITY USING A FITNESS TRACKING DEVICE

CROSS-REFERENCE TO RELATED APPLICATIONS

This application is a continuation application of U.S. patent application Ser. No. 15/674,966, filed Aug. 11, 2017, the disclosure of which is hereby incorporated by reference in its entirety.

BACKGROUND OF THE INVENTION

Field of the Invention

This invention relates to tracking user wellness activity and, in one particular embodiment, to a system and method for tracking wellness activity using a fitness tracking device.

Description of Related Art

An increasing number of people in today's society are becoming health conscious and attempting to live healthier by improving their daily habits, such as by working out, getting more sleep, or eating healthier. Some of these individuals adopt this more health conscious lifestyle without any added motivation required. Still others have the desire to adopt a more health conscious lifestyle but would benefit from incentives urging them to do so.

Fitness tracking devices enable individuals to track their daily activity in order to monitor their health progress. These fitness tracking devices can be worn by individuals throughout the day and can collect wellness data useful for monitoring healthy behavior. These fitness tracking devices provide individuals with instant feedback regarding the wellness data to help them ensure they are living the healthy lifestyle they desire.

Goal-setting is another technique used by many individuals in an attempt to live healthier. Individuals set personal goals as benchmarks by which they can monitor their progress, with the aim to fulfill these goals. However, for those not familiar with diet and exercise science, it may be difficult to determine which goals are realistically achievable or indicative of living healthy.

Therefore, there is a need in the art for a new, improved way of tracking and incentivizing individual wellness activity, such that the individuals are both motivated to implement and rewarded for daily behavior that leads to a longer, healthier life.

SUMMARY OF THE INVENTION

Accordingly, it is an object of the present invention to provide a system and method for tracking and incentivizing wellness activity that overcomes some or all of the deficiencies of the prior art.

According to a non-limiting embodiment or aspect, provided is a method for tracking and incentivizing wellness activity using a fitness tracking device including: receiving, with at least one processor, user wellness data collected over a time period from at least one fitness tracking device of a user, the user wellness data including at least one wellness metric corresponding to the user; analyzing, with at least one processor, user transaction data including transactions initiated by the user with a portable financial device over the time period; automatically determining, with at least one processor, a wellness award for the user based at least partially on the user wellness data and the user transaction data for the time period; and automatically initiating the wellness award for the user.

In one non-limiting embodiment or aspect, the wellness metric may include at least one of the following: steps taken, calories burned, weight lost, distance travelled, calories consumed, fluids consumed, floors climbed, time active, heart rate, sleep duration, or any combination thereof. The method may include assigning to the at least one wellness metric at least one rewards structure, the at least one rewards structure corresponding at least one award to the at least one wellness metric over the time period. The wellness award for the user for the time period may be determined based at least partially on the at least one rewards structure. The wellness metric may include a user wellness goal generated by the user where the wellness award is automatically initiated for the user in response to completion of the user wellness goal. The wellness award may be automatically initiated for the user in response to the user wellness goal receiving approval. The wellness metric may include a suggested wellness goal generated by at least one processor. The suggested wellness goal may be generated based at least partially on historical user wellness data. The suggested wellness goal may be generated based at least partially on historical user transaction data.

In one non-limiting embodiment or aspect, the wellness award may include at least one of the following: statement credit, cash back, cash back for purchases at a merchant, cash back for purchases in a market category, a gift card for a merchant, a gift card for a market category, loyalty rewards for a merchant, a coupon for a merchant, a coupon for a market category, a free product or service, or any combination thereof. The time period may be at least one of the following: a day, a week, a month, three months, six months, a year, or any combination thereof. The time period may be a day, and an ending of the day may be determined based at least partially on the user wellness data. The at least one fitness tracking device may be at least one of the following: a wearable fitness device, a smartphone, a smartwatch, a heartrate monitor, a pedometer, a global positioning system (GPS), or any combination thereof.

According to another non-limiting embodiment or aspect, provided is a system for tracking and incentivizing wellness activity using a fitness tracking device, including at least one server computer including at least one processor programmed and/or configured to: receive user wellness data collected over a time period from at least one fitness tracking device of a user, the user wellness data including at least one wellness metric corresponding to the user; analyze user transaction data including transactions initiated by the user with a portable financial device over the time period; automatically determine, with at least one processor, a wellness award for the user based at least partially on the user wellness data and the user transaction data for the time period; and automatically initiate the wellness award for the user.

In one non-limiting embodiment or aspect, the wellness metric may include at least one of the following: steps taken, calories burned, weight lost, distance travelled, calories consumed, fluids consumed, floors climbed, time active, heart rate, sleep duration, or any combination thereof. The at least one server computer may be further programmed and/or configured to assign to the at least one wellness metric at least one rewards structure, the at least one rewards structure corresponding at least one award to the at least one wellness metric over the time period. The wellness award for the user for the time period may be determined based at least partially on the at least one rewards structure. The wellness metric may include a user wellness goal generated by the user, wherein the wellness award is automatically initiated for the user in response to completion of the user wellness goal. The wellness award may be automatically initiated for the user in response to the user wellness goal receiving approval. The wellness metric may include a suggested wellness goal generated by at least one processor. The suggested wellness goal may be generated based at least partially on historical user wellness data. The suggested wellness goal may be generated based at least partially on historical user transaction data.

In one non-limiting embodiment or aspect, the wellness award may include at least one of the following: statement credit, cash back, cash back for purchases at a merchant, cash back for purchases in a market category, a gift card to a merchant, a gift card for a market category, loyalty rewards to a merchant, a coupon to a merchant, a coupon for a market category, a free product or service, or any combination thereof. The time period may be at least one of the following: a day, a week, a month, three months, six months, a year, or any combination thereof. The time period may be a day, and an ending of the day may be determined based at least partially on the user wellness data. The at least one fitness tracking device may be at least one of the following: a wearable fitness device, a smartphone, a smartwatch, a heartrate monitor, a pedometer, a global positioning system (GPS), or any combination thereof.

According to another non-limiting embodiment or aspect, provided is a method for tracking and incentivizing wellness activity including: analyzing, with at least one processor, historical user transaction data corresponding to a user, the historical user transaction data including transactions previously initiated by the user with a portable financial device; generating, with at least one processor, a suggested user wellness activity to be completed over a time period based at least partially on the historical user transaction data; analyzing, with at least one processor, relevant user transaction data including transactions initiated by the user with the portable financial device over the time period; in response to completion of the wellness activity by the user, automatically determining, with at least one processor, a wellness award for the user based at least partially on the relevant user transaction data for the time period; and automatically initiating the wellness award for the user.

Further embodiments or aspects are set forth in the following numbered clauses:

Clause 1: A method for tracking and incentivizing wellness activity using a fitness tracking device comprising: receiving, with at least one processor, user wellness data collected over a time period from at least one fitness tracking device of a user, the user wellness data comprising at least one wellness metric corresponding to the user; analyzing, with at least one processor, user transaction data comprising transactions initiated by the user with a portable financial device over the time period; automatically determining, with at least one processor, a wellness award for the user based at least partially on the user wellness data and the user transaction data for the time period; and automatically initiating the wellness award for the user.

Clause 2: The method of clause 1, wherein the wellness metric comprises at least one of the following: steps taken, calories burned, weight lost, distance travelled, calories consumed, fluids consumed, floors climbed, time active, heart rate, sleep duration, or any combination thereof.

Clause 3: The method of clause 1 or 2, further comprising assigning to the at least one wellness metric at least one rewards structure, the at least one rewards structure corresponding at least one award to the at least one wellness metric over the time period, wherein the wellness award for the user for the time period is determined based at least partially on the at least one rewards structure.

Clause 4: The method of any of clauses 1-3, wherein the wellness metric comprises a user wellness goal generated by the user, wherein the wellness award is automatically initiated for the user in response to completion of the user wellness goal.

Clause 5: The method of any of clauses 1-4, wherein the wellness award is automatically initiated for the user in response to the user wellness goal receiving approval.

Clause 6: The method of any of clauses 1-5, wherein the wellness metric comprises a suggested wellness goal generated by at least one processor.

Clause 7: The method of any of clauses 1-6, wherein the suggested wellness goal is generated based at least partially on historical user wellness data.

Clause 8: The method of any of clauses 1-7, wherein the suggested wellness goal is generated based at least partially on historical user transaction data.

Clause 9: The method of any of clauses 1-8, wherein the wellness award comprises at least one of the following: statement credit, cash back, cash back for purchases at a merchant, cash back for purchases in a market category, a gift card for a merchant, a gift card for a market category, loyalty rewards for a merchant, a coupon for a merchant, a coupon for a market category, a free product or service, or any combination thereof.

Clause 10: The method of any of clauses 1-9, wherein the time period is at least one of the following: a day, a week, a month, three months, six months, a year, or any combination thereof.

Clause 11: The method of any of clauses 1-10, wherein the time period is a day, and wherein an ending of the day is determined based at least partially on the user wellness data.

Clause 12: The method of any of clauses 1-11, wherein the at least one fitness tracking device comprises at least one of the following: a wearable fitness device, a smartphone, a smartwatch, a heartrate monitor, a pedometer, a global positioning system (GPS), or any combination thereof.

Clause 13: A system for tracking and incentivizing wellness activity using a fitness tracking device, comprising at least one server computer including at least one processor programmed and/or configured to: receive user wellness data collected over a time period from at least one fitness tracking device of a user, the user wellness data comprising at least one wellness metric corresponding to the user; analyze user transaction data comprising transactions initiated by the user with a portable financial device over the time period; automatically determining, with at least one processor, a wellness award for the user based at least partially on the user wellness data and the user transaction data for the time period; and automatically initiate the wellness award for the user.

Clause 14: The system of clause 13, wherein the wellness metric comprises at least one of the following: steps taken, calories burned, weight lost, distance travelled, calories consumed, fluids consumed, floors climbed, time active, heart rate, sleep duration, or any combination thereof.

Clause 15: The system of clause 13 or 14, wherein the at least one server computer is further programmed and/or configured to assign to the at least one wellness metric at least one rewards structure, the at least one rewards structure corresponding at least one award to the at least one wellness metric over the time period, wherein the wellness award for the user for the time period is determined based at least partially on the at least one rewards structure.

Clause 16: The system of any of clauses 13-15, wherein the wellness metric comprises a user wellness goal generated by the user, wherein the wellness award is automatically initiated for the user in response to completion of the user wellness goal.

Clause 17: The system of any of clauses 13-16, wherein the wellness award is automatically initiated for the user in response to the user wellness goal receiving approval.

Clause 18: The system of any of clauses 13-17, wherein the wellness metric comprises a suggested wellness goal generated by at least one processor.

Clause 19: The system of any of clauses 13-18, wherein the suggested wellness goal is generated based at least partially on historical user wellness data.

Clause 20: The system of any of clauses 13-19, wherein the suggested wellness goal is generated based at least partially on historical user transaction data Clause 21: The system of any of clauses 13-20, wherein the wellness award comprises at least one of the following: statement credit, cash back, cash back for purchases at a merchant, cash back for purchases in a market category, a gift card for a merchant, a gift card for a market category, loyalty rewards for a merchant, a coupon for a merchant, a coupon for a market category, a free product or service, or any combination thereof.

Clause 22: The system of any of clauses 13-21, wherein the time period is at least one of the following: a day, a week, a month, three months, six months, a year, or any combination thereof.

Clause 23: The system of any of clauses 13-22, wherein the time period is a day, and wherein an ending of the day is determined based at least partially on the user wellness data.

Clause 24: The system of any of clauses 13-23, wherein the at least one fitness tracking device comprises at least one of the following: a wearable fitness device, a smartphone, a smartwatch, a heartrate monitor, a pedometer, a global positioning system (GPS), or any combination thereof.

Clause 25: A method for tracking and incentivizing wellness activity comprising: analyzing, with at least one processor, historical user transaction data corresponding to a user, the historical user transaction data comprising transactions previously initiated by the user with a portable financial device; generating, with at least one processor, a suggested user wellness activity to be completed over a time period based at least partially on the historical user transaction data; analyzing, with at least one processor, relevant user transaction data comprising transactions initiated by the user with the portable financial device over the time period; in response to completion of the wellness activity by the user, automatically determining, with at least one processor, a wellness award for the user based at least partially on the relevant user transaction data for the time period; and automatically initiating the wellness award for the user.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a," "an," and "the" include plural referents unless the context clearly dictates otherwise.

BRIEF DESCRIPTION OF THE DRAWINGS

Additional advantages and details of the invention are explained in greater detail below with reference to the exemplary embodiments that are illustrated in the accompanying schematic figures, in which:

FIG. 3 is an example of a rewards structure used in one non-limiting embodiment or aspect of a system for tracking and incentivizing wellness activity according to principles of the present invention;

FIG. 4A is an example of user-generated wellness goals used in one non-limiting embodiment or aspect of a system for tracking and incentivizing wellness activity according to principles of the present invention;

FIG. 4B is an example of system-generated wellness goals used in one non-limiting embodiment or aspect of a system for tracking and incentivizing wellness activity according to principles of the present invention;

DESCRIPTION OF THE INVENTION

Figure 1:
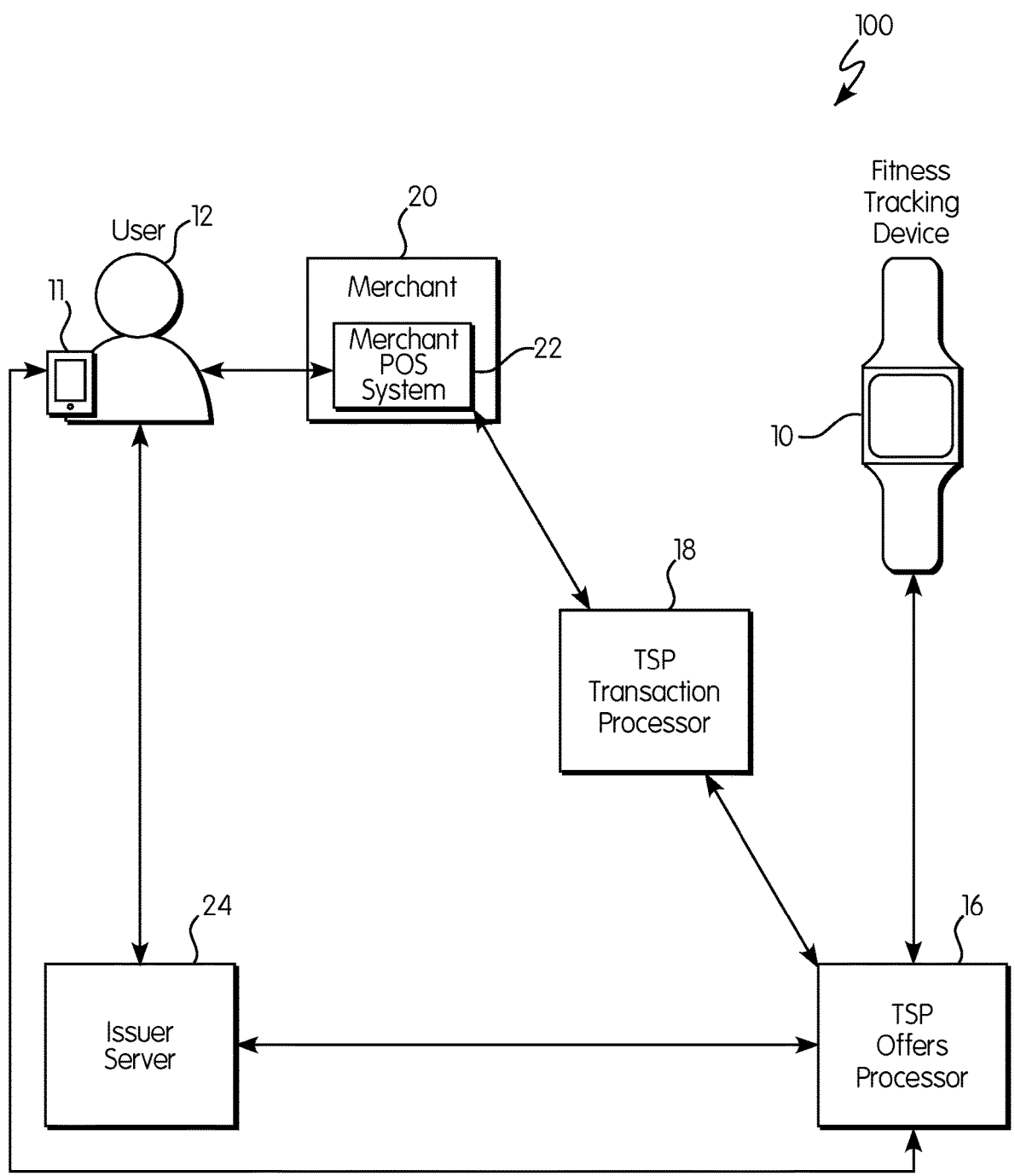
FIG. 1 is a schematic diagram of one non-limiting embodiment or aspect of a system for tracking and incentivizing wellness activity according to principles of the present invention.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

As used herein, the terms "issuing institution," "portable financial device issuer," "issuer," or "issuer bank" may refer to one or more entities that provide accounts to customers for conducting payment transactions, such as initiating credit and/or debit payments. For example, an issuing institution may provide an account identifier, such as a personal account number (PAN), to a customer that uniquely identifies one or more accounts associated with that customer. The account identifier may be embodied on a portable financial device such as a physical financial instrument, e.g., a payment card, and/or may be electronic and used for electronic payments. As used herein, the term "account identifier" may include one or more PANs, tokens, or other identifiers associated with a customer account. The term "token" may refer to an identifier that is used as a substitute or replacement identifier for an original account identifier, such as a PAN. Account identifiers may be alphanumeric or any combination of characters and/or symbols. Tokens may be associated with a PAN or other original account identifier in one or more databases such that they may be used to conduct a transaction without directly using the original account identifier. In some examples, an original account identifier, such as a PAN, may be associated with a plurality of tokens for different individuals or purposes. An issuing institution may be associated with a bank identification number (BIN) that uniquely identifies it. The terms "issuer" and "issuer server" may also refer to one or more computer systems operated by or on behalf of an issuing institution, such as a server computer executing one or more software applications. For example, an issuing institution system may include one or more authorization servers for authorizing a payment transaction.

As used herein, the term "merchant" refers to an individual or entity that provides goods and/or services, or access to goods and/or services, to customers (also referred to herein interchangeably as a "consumer") based on a transaction, such as a payment transaction. "Merchant" may also refer to one or more computer systems operated by or on behalf of a merchant, such as a server computer executing one or more software applications. As used herein, a "merchant point-of-sale (POS) system" may refer to one or more computers and/or peripheral devices used by a merchant to engage in payment transactions with customers, including one or more card readers, near-field communication (NFC) receivers, RFID receivers, and/or other contactless transceivers or receivers, contact-based receivers, payment terminals, computers, servers, input devices, and/or other like devices that may be used to initiate a payment transaction. A merchant point-of-sale system may also include one or more server computers programmed or configured to process online payment transactions through webpages, mobile applications, and/or the like.

As used herein, the term "transaction service provider" may refer to an entity that receives transaction authorization requests from merchants or other entities and provides guarantees of payment, in some cases through an agreement between the transaction service provider and the issuing institution. The term "transaction service provider" may also refer to one or more computer systems operated by or on behalf of a transaction service provider, such as a transaction processing server executing one or more software applications. A transaction processing server may include one or more processors and, in some non-limiting embodiments or aspects, may be operated by or on behalf of a transaction service provider.

As used herein, the term "portable financial device" may refer to a payment card (e.g., a credit or debit card), a gift card, a smartcard, smart media, a payroll card, a healthcare card, a wrist band, a machine-readable medium containing account information, a keychain device or fob, an RFID transponder, a retailer discount or loyalty card, a cellular phone, an electronic wallet application, a personal digital assistant, a pager, a security card, a computer, an access card, a wireless terminal, and/or a transponder, as examples. The portable financial device may include a volatile or a non-volatile memory to store information, such as an account identifier or a name of the account holder.

As used herein, the term "server" may refer to or include one or more processors or computers, storage devices, or similar computer arrangements that are operated by or facilitate communication and processing for multiple parties in a network environment, such as the internet, although it will be appreciated that communication may be facilitated over one or more public or private network environments and that various other arrangements are possible. Further, multiple computers, e.g., servers, or other computerized devices, e.g., point-of-sale devices, directly or indirectly communicating in the network environment may constitute a "system," such as a merchant's point-of-sale system.

Non-limiting embodiments or aspects of the present invention are directed to a system and method for tracking and incentivizing wellness activity using a fitness tracking device. Non-limiting embodiments or aspects of the invention allow users of a portable financial device to be rewarded and incentivized for their wellness activity. The users may fulfill wellness goals generated by and/or for them by tracking their health-related spending and/or health-related physical activity over a time period. For fulfilling their wellness goals, the user may receive a wellness award, such as cash back and/or statement credit for purchases made during the time period. In some examples, a fitness tracking device collects user wellness data including at least one wellness metric for a user. At least one processor receives the user wellness data collected by the fitness tracking device. The processor analyzes user transactions data including transactions initiated by the user with their portable financial device over a time period. The processor is able to then automatically determine a wellness award for the user based on the user wellness data and the user transaction data to automatically initiate a wellness award for the user. Thus, the processor is able to provide wellness awards to users based at least partially on their user wellness data and user transaction data, such that the user is provided with further incentives live healthier by performing further wellness activity.

Referring to FIG. 1, a system 100 for tracking and incentivizing wellness activity is shown according to a non-limiting embodiment or aspect. A fitness tracking device 10 may be included that corresponds to a user 12. In some non-limiting embodiments or aspects, the fitness tracking device 10 may be wearable by the user 12. The fitness tracking device 10 may be worn anywhere on the user 12, such as on the user's wrist, head, neck, torso, waist, ankle, and the like, to enable the fitness tracking device 10 to collect physiological data regarding the user 12. The user 12 may be an individual that uses a portable financial device to initiate transactions. In some non-limiting embodiments or aspects, the portable financial device is loaded on the fitness tracking device 10 such that the fitness tracking device 10 may be used to initiate transactions.

Figure 2:
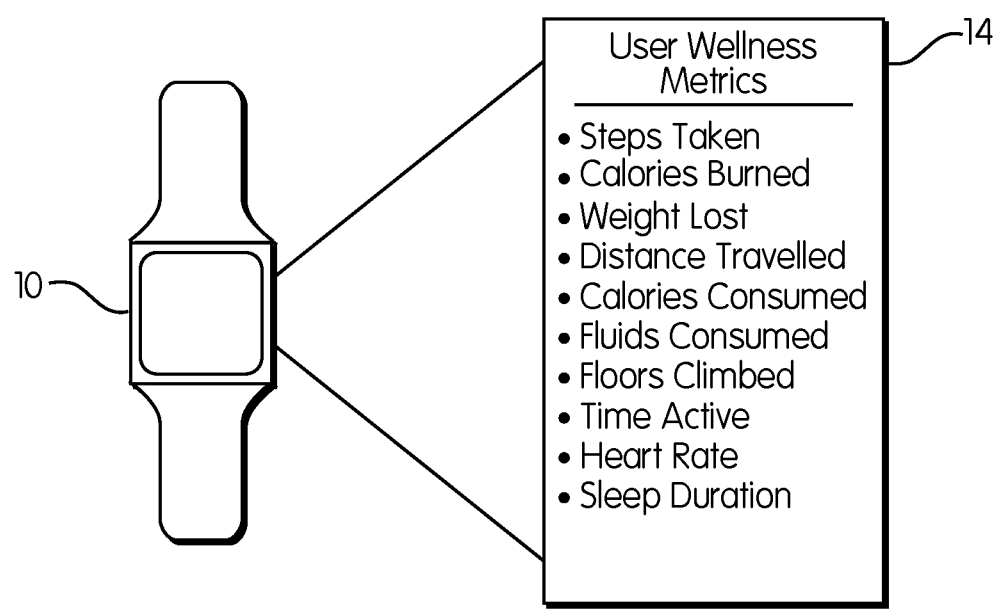
FIG. 2 is an example of a fitness tracking device used in one non-limiting embodiment or aspect of a system for tracking and incentivizing wellness activity according to principles of the present invention.

With continued reference to FIG. 1 and referring to FIG. 2, the fitness tracking device 10 may collect user wellness data, the user wellness data including user wellness metrics 14. User wellness metrics 14 may be metrics that are associated with tracking and/or monitoring the user's 12 overall health and/or may indicate healthy or unhealthy activity of the user 12. User wellness metrics 14 may include one or more of: steps taken, calories burned, weight lost, distance travelled, calories consumed, fluids consumed, floors climbed, time active, heart rate, and sleep duration. However, it will be appreciated that other data may be collected by the fitness tracking device 10 in addition to the user wellness metrics 14, such as data related to the health and/or activity of the user 12.

With continued reference to FIG. 1 and FIG. 2, the fitness tracking device 10 may be any kind of device suitable for collecting user wellness data. In some non-limiting embodiments or aspects, the fitness tracking device 10 is a wearable fitness device, a mobile device (e.g., smartphone or portable computer), a smartwatch, a heartrate monitor, a pedometer, a global positioning system (GPS), and the like. For example, the mobile device may include accelerometers and/or gyroscopes to enable collection of user wellness data. However, it will be appreciated that the fitness tracking device 10 is not limited to these devices and may be any device capable of collecting user wellness data.

With continued reference to FIG. 1, the fitness tracking device 10 may be in communication with a transaction service provider offers processor 16 (hereinafter "offers processor"). The offers processor 16 may be a component of a transaction processing server managed by or on behalf of a transaction service provider. In some non-limiting embodiments or aspects, the offers processor 16 is in communication with a server in communication with the fitness tracking device 10. The offers processor 16 may be managed by or on behalf of the transaction service provider. The offers processor 16 may be located at or remote from the transaction service provider. The offers processor 16 may execute functions related to offers programs facilitated by or provided by the transaction service provider or issuer.

With continued reference to FIG. 1, in some non-limiting embodiments or aspects, the offers processor 16 may receive user wellness data (including the user wellness metrics 14) collected by the fitness tracking device 10 over a time period. In some non-limiting embodiments or aspects, the offers processors receives the user wellness data by receiving a communication from the fitness tracking device 10 (or server in communication with the fitness tracking device 10). In other non-limiting embodiments or aspects, the offers processor 16 may receive the user wellness data by transmitting a communication to the fitness tracking device 10 (or server in communication with the fitness tracking device 10), which, in response, communicates the user wellness data to the offers processor 16. The user wellness data may be received by the offers processor 16 from the fitness tracking device 10 after a predetermined time period. The time period may be in increments of minutes, hours, days, weeks, years, and the like. The time period may be one day, one week, one month, three months, six months, one year, and the like. In some non-limiting embodiments or aspects, the user wellness data may be received by the offers processor 16 from the fitness tracking device 10 at the end of each day. The user wellness data may be passively received, received in response to a request, received by being retrieved, and the like.

With continued reference to FIG. 1, in some non-limiting embodiments or aspects, the time period may be one day. For example, the user wellness metric 14 may include the count of steps by the user 12 over the course of a single day. In some non-limiting embodiments or aspects, the length of the day may be the same for all users, for instance a twenty-four hour time period. In this non-limiting embodiment or aspect, the user wellness metric 14 may be received for the previous twenty-four hours at 00:00:01 AM Greenwich Mean Time (GMT) (or other control time zone). In other non-limiting embodiments or aspects, the user wellness data may be received at a specific time based on the time zone the fitness tracking device 10 is located. For instance, for a user living in Pittsburgh, Pa. (whose fitness tracking device 10 is also located therein), the user wellness data may be received for the previous twenty-four hours at 00:00:01 AM Eastern Time (Eastern Standard Time or Eastern Daylight Time, as applicable). In other non-limiting embodiments or aspects, the length of the day is customized for the user 12. For example, the fitness tracking device 10 may collect data corresponding to the sleeping activity of the user 12. From this sleep activity, the length of a day for the specific user 12 may be determined based on when the user 12 awoke and when the user 12 went to sleep that day or an average of previous sleep activity. Sleep activity may constitute user wellness data. Therefore, the length of the day for each user may be based at least partially on the user wellness data. The time period for each user may be based at least partially on the user wellness data.

With continued reference to FIG. 1, the offers processor 16 may be in communication with a transaction service provider transaction processor 18 (hereinafter "transaction processor"). The transaction processor 18 may be a component of the transaction processing server. The transaction processor 18 may be managed by or on behalf of a transaction service provider. The transaction processor 18 may be located at or remote from the transaction service provider. The transaction processor 18 may execute functions related to transactions initiated by a portable financial device of the user 12 managed by or on behalf of the transaction service provider. The transaction processor 18 may be a processor separate from the offers processor 16. In some non-limiting embodiments or aspects, the transaction processor 18 and the offers processor 16 are the same processor or processors.

With continued reference to FIG. 1, the transaction processor 18 may be in communication with a merchant system 20, such as a merchant point-of-sale system 22. The merchant point-of-sale system 22 may communicate transaction data to the transaction processor 18, and the transaction data may correspond to data associated with transactions conducted between the merchant point-of-sale system 22 and the user 12. The transaction may be conducted between the merchant point-of-sale system 22 and a user device 11. The user device 11 may be any electronic device, such as a computer, laptop computer, tablet computer, smartphone, cellular phone, smartwatch, and the like. For instance, the transaction data may be associated with a purchase of goods and/or services. The transaction may be initiated between the user 12 and the merchant point-of-sale system 22 using the user's 12 portable financial device. The transaction processor 18 may be in communication with a plurality of merchant systems for which it has a business relationship and may receive transaction data from each of those merchants' point-of-sale systems for transactions conducted using the portable financial device of the user 12. The transaction processor 18 may communicate the transaction data to the offers processor 16. The transaction processor 18 may communicate transaction data of the user 12 including transactions initiated by a portable financial device over a time period to the offers processor 16. The offers processor 16 may analyze this user transaction data.

The transaction data communicated by the merchant point-of-sale system 22 to the transaction processor 18 may include data related to the transactions between the merchant point-of-sale system 22 and the user 12. Non-limiting examples of transaction data that may be communicated by the merchant point-of-sale system 22 to the transaction processor 18 may include: user name, personal information of the user (e.g., home address, billing address, social security number, driver's license number, telephone number, email address, credit score, credit score history, and the like), user's portable financial device account identifier (e.g., 16 digit PAN), another account identifier, goods and/or services purchased, type of goods and/or services purchased, quantity of goods and/or services purchased, barcode data and/or unique identifier(s) corresponding to the goods and/or services purchased, merchant name, merchant identification number, merchant address and other contact information, location of sale, point-of-sale details, acquirer details (e.g., acquirer bank identification number (BIN)), and the like. However, it will be appreciated that the transaction data may include any information required for processing the transaction. Further, it will be appreciated that the transaction data may, in some non-limiting embodiments or aspects, be communicated from the merchant point-of-sale system 22 to the transaction processor 18 through an intermediary, such as from an acquirer system or a payment facilitator system.

With continued reference to FIG. 1, the offers processor 16 may be in communication with an issuer server 24 managed by or on behalf of an issuer. The offers processor 16 may transmit data to or receive data from the issuer server 24 associated with offers programs being provided by the issuer and facilitated by the offers processor 16 or offers programs being provided by the transaction service provider. An offers program may be a program provided by the transaction service provider and/or the issuer which offers the user 12 an award for a certain wellness activity, including threshold(s) of the wellness activity. In some non-limiting embodiments or aspects, the offers program provides the user 12 a wellness award based at least partially on wellness activity corresponding to the wellness data collected by the user's 12 fitness tracking device 10. The wellness award may also be based at least partially on wellness activity that corresponds to wellness data that includes user transaction data from the transaction processor 18. In some non-limiting embodiments or aspects, the offers program provides the user 12 the wellness award based at least partially on wellness activity corresponding to wellness data received from a third-party source.

With continued reference to FIG. 1, in some non-limiting embodiments or aspects, the wellness award from the offers processor 16 and/or the issuer server 24 may be determined by the offers processor 16 after analyzing the user transaction data. The offers processor 16 may automatically determine the wellness award associated with the offer based at least partially on the user wellness data (e.g., from the fitness tracking device 10) and/or the historical user transaction data (e.g., from the transaction processor 18) for the time period in combination with the amount of spending with the portable financial device over the time period.

In some non-limiting embodiments or aspects, the wellness award may associate an award with at least one wellness metric from the user wellness data collected by the fitness tracking device 10. For example, the wellness award may be associated with achieving a certain number of steps over a time period (e.g., a day). It will be appreciated that the wellness award may be achieved in connection with any of the previously-described user wellness metrics over any of the previously-described time periods.

In some non-limiting embodiments or aspects, the wellness award may associate an award with some wellness activity not collected by the fitness tracking device 10. For example, the wellness award may be associated with a wellness activity associated with transactions conducted by the user 12, in which case the transaction processor 18 may provide the relevant transaction data associated with the wellness activity that the wellness award is associated with. For example, the wellness activity may include a wellness award for spending on healthy purchases, such as purchases of healthy foods, health products, fitness products, fitness devices, gym memberships, race and competition entries, and the like, as determined by merchant category codes, merchant identifiers, and the like. The wellness award may be associated with any type of activity, physical or otherwise, that is related to the health or fitness of the user 12.

The wellness award provided to the user 12 from the offers processor 16 or the issuer server 24 may be in any form. In some non-limiting embodiments or aspects, the wellness award applied to the user's 12 account includes at least one of: statement credit, cash back, cash back for purchases at a merchant, cash back for purchases in a market category, a gift card for a merchant, a gift card for a market category, loyalty rewards for a merchant, a coupon for a merchant, a coupon for a market category, a free product or service, or any combination thereof. In some non-limiting embodiments or aspects, the wellness award may be communicated to the user device 11.

With continued reference to FIG. 1, in some non-limiting embodiments or aspects, the offers processor 16 automatically initiates the wellness award earned by the user 12. The offers processor 16 may communicate data regarding the wellness award to the issuer server 24, such that the wellness award associated with the offer from the issuer may be applied to an account of the user 12. In some non-limiting embodiments or aspects, the offer may be an offer to the user 12 from the transaction service provider. In this non-limiting embodiment or aspect, the offers processor 16 may communicate with the issuer server 24 to apply the wellness award associated with the transaction service provider offer to the user's 12 account. In other non-limiting embodiments or aspects, the offers processor 16 may apply the wellness award to the user's 12 account directly.

Referring to FIG. 3, an example of a rewards structure 26 used in the system 100 for tracking and incentivizing wellness activity is shown. A rewards structure 26 may include one or more data structures associating wellness activity and wellness metrics with wellness awards. In some non-limiting embodiments or aspects, the rewards structure 26 assigns a wellness activity at least one award over the time period. The wellness award may be determined at least partially based on the rewards structure 26. In some non-limiting examples, the rewards structure 26 associates a certain threshold of the wellness activity (e.g., the previously-described physical wellness metrics 14, health-related purchases, or other health-related activity) with a certain percentage of the previously-listed types of the wellness award (e.g., cash back or statement credit). In the example shown in FIG. 3, the wellness activity may be the user wellness metric 14 of a daily step count, and a wellness award of a certain percentage of cash back may be assigned to different thresholds of daily steps. In this example, a user taking 5,000-9,999 steps receives 1% cashback for purchases made over the time period (e.g., a day), a user taking 10,000-14,999 steps receives 2% cashback for purchases made over the time period, a user taking 15,000-19,999 steps receives 2.5% cashback for purchases made over the time period, a user taking 20,000-24,999 steps receives 3% cashback for purchases made over the time period, a user taking 25,000-29,999 steps receives 3.5% cashback for purchases made over the time period, and a user taking 30,000+ steps receives 4% cashback for purchases made over the time period. In an example in which a user spends $100 over the time period and takes 7,500 steps over the time period, the wellness award amount would be $1.00 (1% of $100).

It will be appreciated that similar rewards structures 26 may be utilized other than the one depicted in FIG. 3. For instance, for wellness activities that do not include thresholds but are either achieved or not achieved (e.g., when the wellness activity is a goal that is either achieved or not achieved), the rewards structure 26 may assign a certain percent cash back for the goal being achieved. It will be appreciated that the rewards structure 26 may be set up in any manner to associate any of the contemplated wellness activities (or combinations of wellness activities) with any of the contemplated wellness awards (or combination of wellness awards).

Referring to FIGS. 4A and 4B, wellness goals 28, 30 representing wellness activities in the system 100 for tracking and incentivizing wellness activity are shown. The wellness goal 28, 30 may be a threshold of previously-described wellness activity (e.g., the previously described physical activity, health-related purchases, or other health-related activity) that must be achieved by the user 12 during the time period in order to receive the assigned wellness award. Achievement of the wellness goal 28, 30 may lead to the user's 12 account receiving a wellness award. In some non-limiting embodiments or aspects, the fitness tracking device 10 may be used to track the activity associated with the wellness goal 28, 30 (e.g., where the wellness goal 28, 30 is associated with an activity tracked by the fitness tracking device 10). In some non-limiting embodiments or aspects, the transaction processor 18 may be used to track the activity associated with the wellness goal 28, 30 (e.g., where the wellness goal 28, 30 is associated with transactions of the user 12). In some non-limiting embodiments or aspects, a third-party system may be used to track the wellness activity associated with the wellness goal 28, 30. The offers processor 16 may communicate with the fitness tracking device 10, the transaction processor 18 and/or the third-party system to determine whether the user 12 achieved the wellness goal 28, 30.

With continued reference to FIG. 4A, in some non-limiting embodiments or aspects, the wellness goal 28 may be generated by the user device 11, and the wellness award may be automatically initiated for the user 12 in response to completion of the wellness goal 28. In this non-limiting embodiment or aspect, the user device 11 may suggest a wellness goal 28 for which the user 12 would receive the wellness award upon successful completion. The user-generated wellness goal 28 may be communicated to the offers processor 16 and/or the issuer server 24 via the user device 11. The offers processor 16 and/or the issuer server 24 may analyze the user-generated wellness goal 28 and either approve or reject the user-generated wellness goal 28, and the wellness award may be automatically initiated after approval and completion of the user-generated wellness goal 28. The offers processor 16 and/or the issuer server 24 may then communicate the status (e.g., approved or rejected) of the user-generated wellness goal 28 to the user device 11. An approved user-generated wellness goal 28 may be pursued by the user 12, and successful completion of the approved user-generated wellness goal 28 may lead to a wellness award being initiated for the user 12. A rejected user-generated wellness goal 28 may not be pursued by the user 12, and no wellness award may be initiated for the user 12 upon successful completion of the rejected user-generated wellness goal 28. The user device 11 may propose a wellness award associated with successful completion of the suggested user-generated wellness goal 28, or the offers processor 16 and/or the issuer server 24 may determine a wellness award for successful completion of the suggested user-generated wellness goal 28. The wellness award may be generated based on the difficulty of the suggested user-generated wellness goal 28 (e.g., higher difficulty means higher wellness award) or based on the health value of the user-generated wellness goal 28 (e.g., a healthier goal means a higher wellness award).

With continued reference to FIG. 4A, examples of user-generated wellness goals 28 are shown. In the first line, the user device 11 communicates a user-generated wellness goal 28 of completing a 5k race in the month of May. The user device 11 communicates this user-generated wellness goal 28 to the offers processor 16 and/or the issuer server 24 for approval. The offers processor 16 and/or the issuer server analyzes this user-generated wellness goal 28 and approves it. The offers processor 16 and/or the issuer server 24 then communicates to the user device 11 that the user-generated wellness goal 28 is approved. The user 12 may pursue the approved user-generated wellness goal 28 over the time period (e.g., one month (May)). The user 12 may receive the wellness award (e.g., 2% cash back for purchases in May) if the user 12 completes a 5k race in May, such as the wellness award being applied to the user's 12 account. It may be determined a number of ways that the user 12 completed a 5k race in May. For example, the fitness tracking device 10 of the user 12 may determine that the user 12 completed a 5k race in May. The transaction processor 18 may determine that the user 12 completed a 5k in May by analyzing transactions initiated by the user 12 to determine if the user 12 paid to sign up for a 5k race held in May. Other third party processors and/or devices may be used to determine whether the user 12 completed the 5k race in May (e.g., a third party website that lists results of the 5k race in which the user 12 participated).

With continued reference to FIG. 4A, not every suggested wellness goal 28 from the user device 11 may be approved by the offers processor 16 and/or the issuer server 24. In the second line of the table, the user device 11 communicates a user-suggested wellness goal 28 of taking at least 2,000 steps every day in May. The offers processor 16 and/or the issuer server 24 may reject this user-suggested wellness goal 28 for reasons such as insufficient difficulty or not being directed to an activity that enhances the overall wellness of the user 12. In the fourth line of the table, the user device 11 communicates a user-suggested wellness goal 28 of being active for at least 30 minutes each day of the upcoming weekend, and this user-suggested wellness goal 28 is communicated to the offers processor 16 and/or the issuer server 24. The user-suggested wellness goal 28 may be automatically approved or rejected, or the user-suggested wellness goal 28 may receive a "pending" status while the user-suggested wellness goal 28 is being analyzed by the offers processor 16, the issuer server 24, and/or by an individual. Once the user-suggested wellness goal 28 is approved or rejected, the pending status will be changed to reflect the new status.

Referring to FIG. 4B, in some non-limiting embodiments or aspects, the wellness goal 30 may be generated by the offers processor 16 and/or the issuer server 24 or by an entity acting on behalf of the transaction service provider and/or the issuer (hereinafter referred to as a system-generated wellness goal 30), and the wellness award may be automatically initiated for the user 12 in response to completion of the system-generated wellness goal 30. Along with the system-generated wellness goal 30, the offers processor 16 and/or the issuer server 24 may provide a wellness award for completion of the system-generated wellness goal 30. In this non-limiting embodiment or aspect, the offers processor 16 and/or the issuer server 24 may suggest a wellness goal 30 for which the user 12 would receive the wellness award upon successful completion. The system-generated wellness goal 30 may be communicated to the user device 11. In some non-limiting embodiments or aspects, the user device 11 may receive the system-generated wellness goals(s) 30 and accept or reject them. An approved system generated wellness goal 30 may be pursued by the user 12, and successful completion of the approved system-generated wellness goal 30 may lead to a wellness award being initiated for the user 12. A rejected system-generated wellness goal 30 may not be pursued by the user 12, and no wellness award may be initiated for the user 12 upon successful completion of the rejected system-generated wellness goal 30. In other non-limiting embodiments or aspects, the user 12 may be automatically enrolled in a system-generated wellness goal 30. For example, the system-generated wellness goal 30 may be a certain count of steps for each day associated with a certain percentage cash back for spending initiated that day, and all users in the offers program may be automatically enrolled in this system-generated wellness goal 30 and automatically receive a wellness award upon successful completion.

With continued reference to FIG. 4B, in the first line, the system-generated wellness goal 30 is for the user 12 to take 10,000 steps for that day. This system-generated wellness goal 30 is generated by an entity other than the user device 11, such as the offers processor 16 and/or the issuer server 24. A 1% cash back for purchases made that day is provided for successful completion of the system-generated wellness goal 30. The user device 11 may accept or reject the system-generated wellness goal 30. The user device 11 may receive multiple system-generated wellness goals 30, and may accept or reject any number of the system-generated wellness goals 30. The system-generated wellness goals 30 may be for a variety of activities directed to the user's 12 wellness for a variety of time periods. In some embodiments or aspects, the user device 11 may accept multiple system-generated wellness goals 30 and receive a wellness award for each one. In some non-limiting embodiments or aspects, system-generated wellness goals 30 may overlap in time period (e.g., multiple wellness goals for the same day, week, month, and the like), and the wellness awards for these completed system-generated wellness goals 30 may be summed. In other non-limiting embodiments or aspects, system-generated wellness goals 30 may overlap in time period (e.g., multiple wellness goals for the same day, week, month, and the like), and the user device 11 may receive a wellness award for only the completed system-generated wellness goal 30 that has the highest wellness award.

With continued reference to FIG. 4B, the system-generated wellness award 30 may be generated for the user 12 based on any sufficient reason. In some non-limiting embodiments or aspects, all users may receive the same system-generated wellness awards 30 to either accept or reject. In other non-limiting embodiments or aspects, the system-generated wellness award 30 may be customized for each user. For example, the system-generated wellness award 30 may be based at least partially on historical wellness data of the user 12 from the user's 12 fitness tracking device 10. The system-generated wellness goal 30 may be generated such that the system-generated wellness goal 30 is the next threshold of difficulty in a certain activity, compared to the historical wellness data. For example, the historical wellness data for the user 12 may indicate that the user 12 takes an average of 7,500 steps/day, so the offers processor 16 and/or issuer server 24 may generate a system-generated wellness goal 30 for the user 12 to increase to 10,000 steps/day. The system-generated wellness goal 30 may be based on similar goals generated for other users with similar thresholds of activity or similar historical user wellness data, such as by using a machine learning algorithm.

In another non-limiting embodiment or aspect, the system-generated wellness award 30 may be generated based at least partially on historical user transaction data collected by the transaction processor 18. The system-generated wellness goal 30 may be generated to incentivize healthy behavior based on the historical user transaction data. For example, the user transaction data may indicate that the user 12 purchases fast food multiple times each week. The system-generated wellness goal 30 may be generated to incentivize the user 12 to decrease the frequency of fast food transactions or to purchase alternative, healthier foods, such as organic foods. The system-generated wellness goal 30 may be based on similar goals generated for other users with similar historical user transaction data, such as by using a machine learning algorithm.

Figure 5:
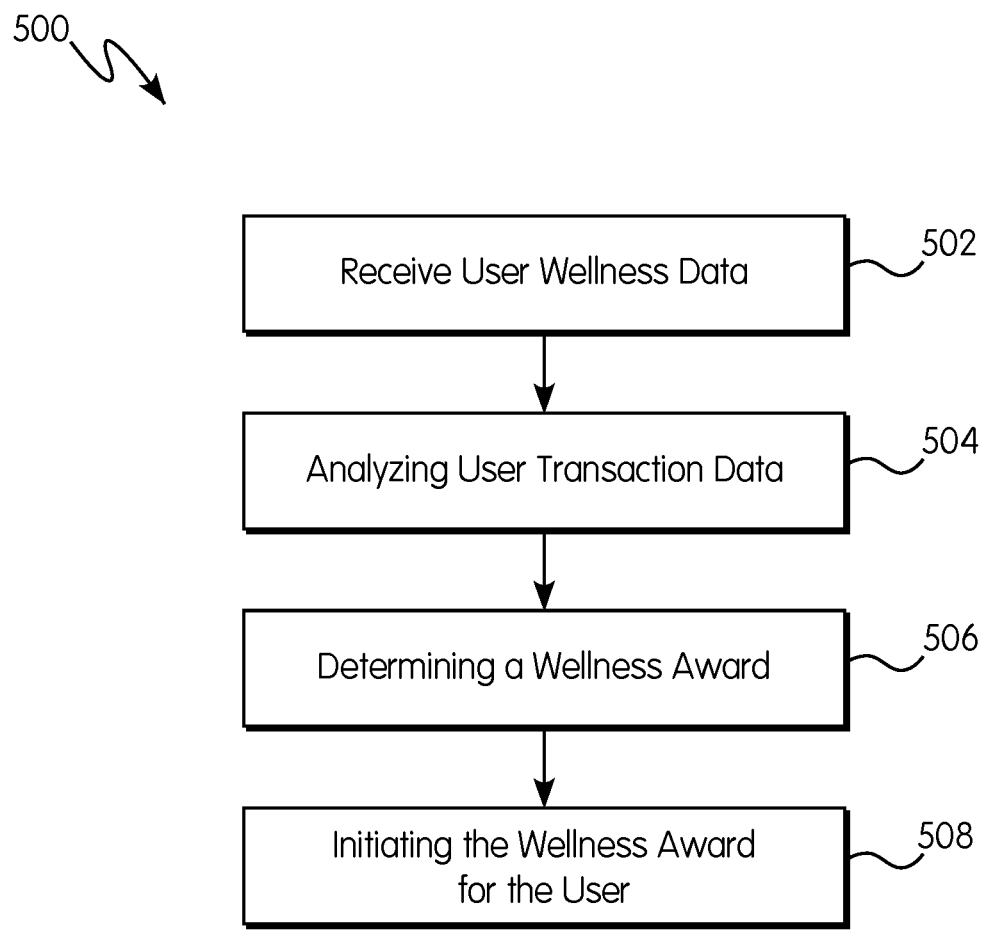
FIG. 5 is a step diagram of one non-limiting embodiment or aspect of a method for tracking and incentivizing wellness activity using a fitness tracking device according to principles of the present invention.

Referring to FIG. 5, a method 500 for tracking and incentivizing wellness activity is shown. At a step 502, the user wellness data collected over a time period may be received with at least one processor (e.g., the offers processor 16). The user wellness data may include any of the previously-described wellness metrics 14. The user wellness data may be received by the offers processor 16 from the fitness tracking device 10. At a step 504, the processor (e.g., the offers processor 16, transaction processor 18, or the issuer server 24) may analyze user transaction data initiated by the user 12 with a portable financial device over the time period time period. At a step 506, the processor (e.g., the offers processor 16 or the issuer server 24) may automatically determine the wellness award for the user 12 based at least partially on the user wellness data and the user transaction data for the time period. At a step 508, the wellness award may be automatically initiated for the user 12. This may include the offers processor 16, the issuer server 24, and/or other entity executing steps such that the wellness award is applied to the user 12 account and/or otherwise communicated to the user 12.

Figure 6:
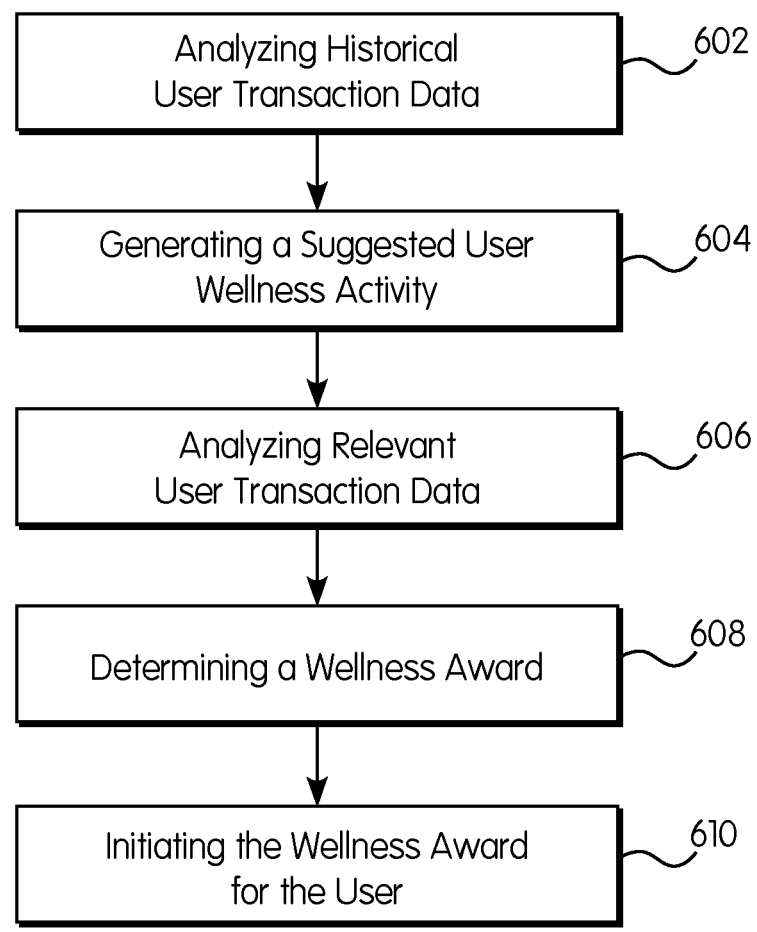
FIG. 6 is a step diagram of one non-limiting embodiment or aspect of a method for tracking and incentivizing wellness activity according to principles of the present invention.

Referring to FIG. 6, a method 600 for tracking and incentivizing wellness activity is shown. At a step 602, historical user transaction data corresponding to the user 12 may be analyzed using at least one processor (e.g., the offers processor 16, transaction processor 18, or the issuer server 24). The historical user transaction data may include transactions previously initiated by the user 12 with a portable financial device. At a step 604, a suggested user wellness activity (e.g., a user-generated wellness goal 28 or a system-generated wellness goal 30) may be generated by at least one processor (e.g., the offers processor 16, transaction processor 18, or the issuer server 24) to be completed over a time period. The user wellness activity may be generated based at least partially on the historical user transaction data. At a step 606, at least one processor (e.g., the offers processor 16, transaction processor 18, or the issuer server 24) may analyze relevant user transaction data including transactions initiated by the user 12 with the portable financial device over the time period. This relevant user transaction data may be distinguishable from the historical user transaction data in that the historical user transaction data may include transactions initiated by the user 12 before the time period, and the relevant user transaction data may include transactions initiated during the time period. At a step 608, at least one processor (e.g., the offers processor 16 or the issuer server 24) may automatically determine the wellness award for the user 12 in response to completion of the user wellness activity for the time period. The wellness award may be determined based at least partially on the relevant user transaction data. At a step 610, the wellness award may be automatically be initiated for the user 12. This may include the offers processor 16, the issuer server 24, and/or other entity executing steps such that the wellness award is applied to the user's 12 account and/or otherwise communicated to the user 12.

Examples

The following examples are provided to illustrate embodiments or aspects of the system and method for tracking and incentivizing wellness activity and are not meant to limit the invention in any way.

Figure 7:
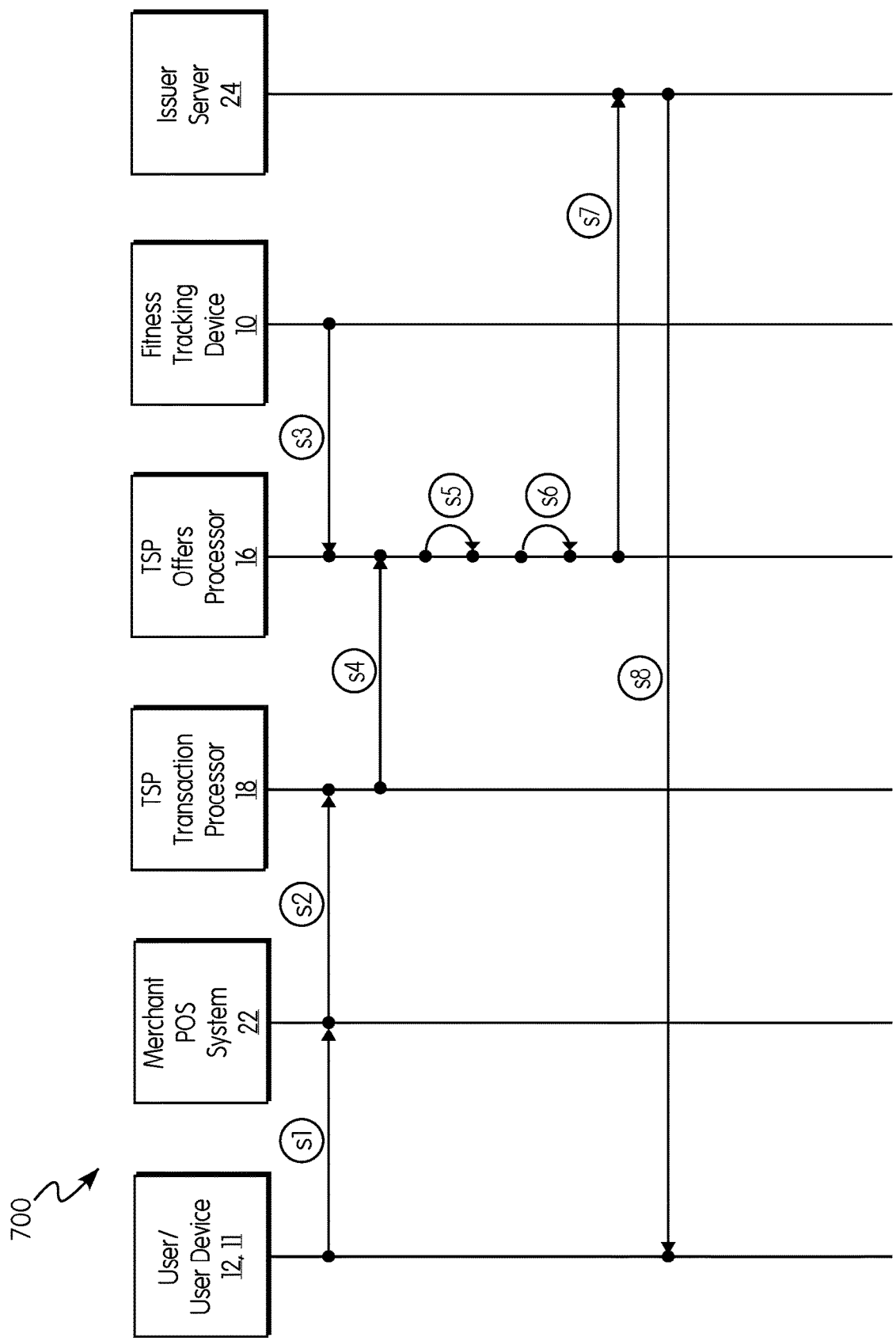
FIG. 7 is a process flow diagram of one non-limiting embodiment or aspect of a method for tracking and incentivizing wellness activity using a fitness tracking device according to principles of the present invention.
Figure 8:
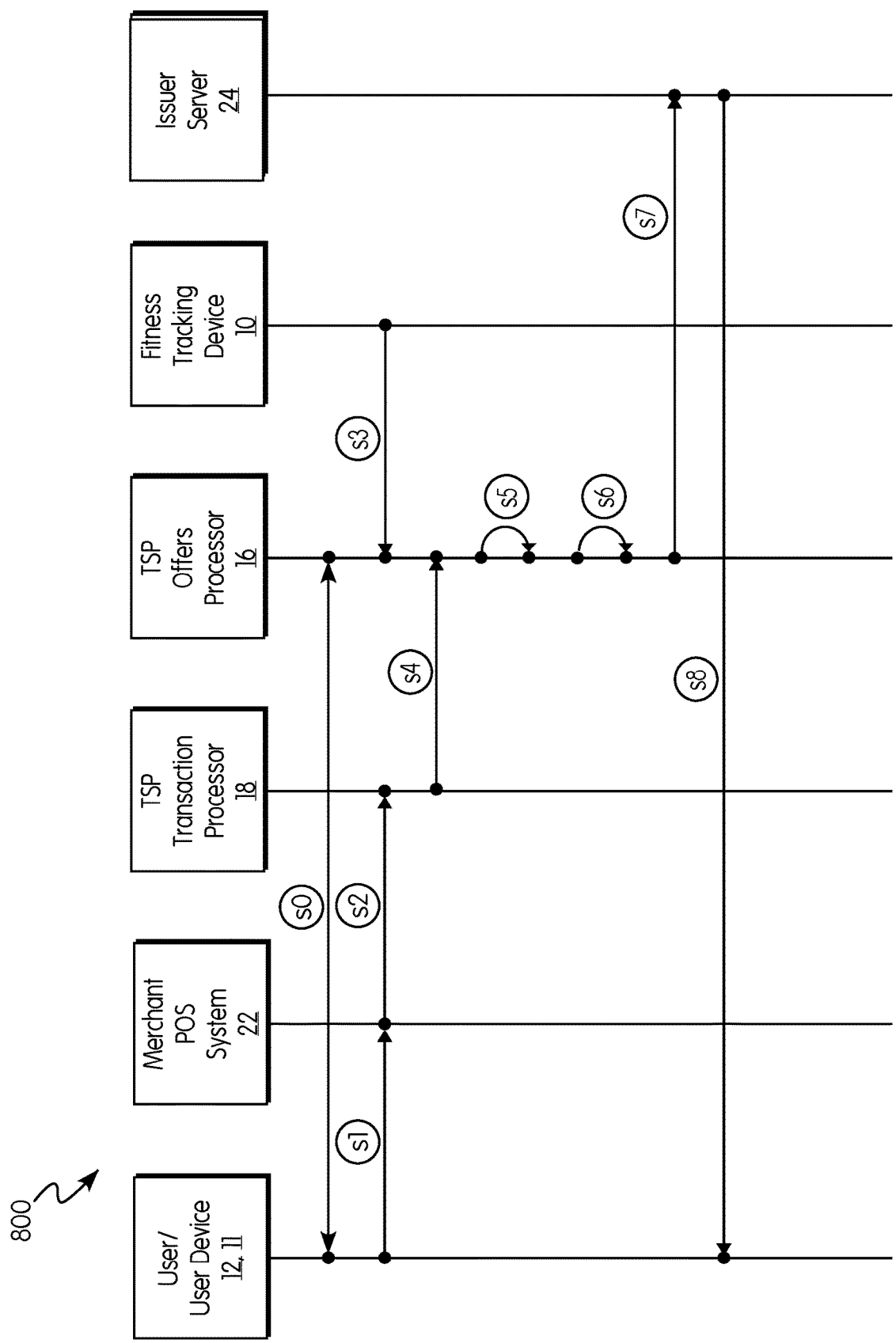
FIG. 8 is a process flow diagram of one non-limiting embodiment or aspect of another method for tracking and incentivizing wellness activity using a fitness tracking device according to principles of the present invention.
Figure 9:
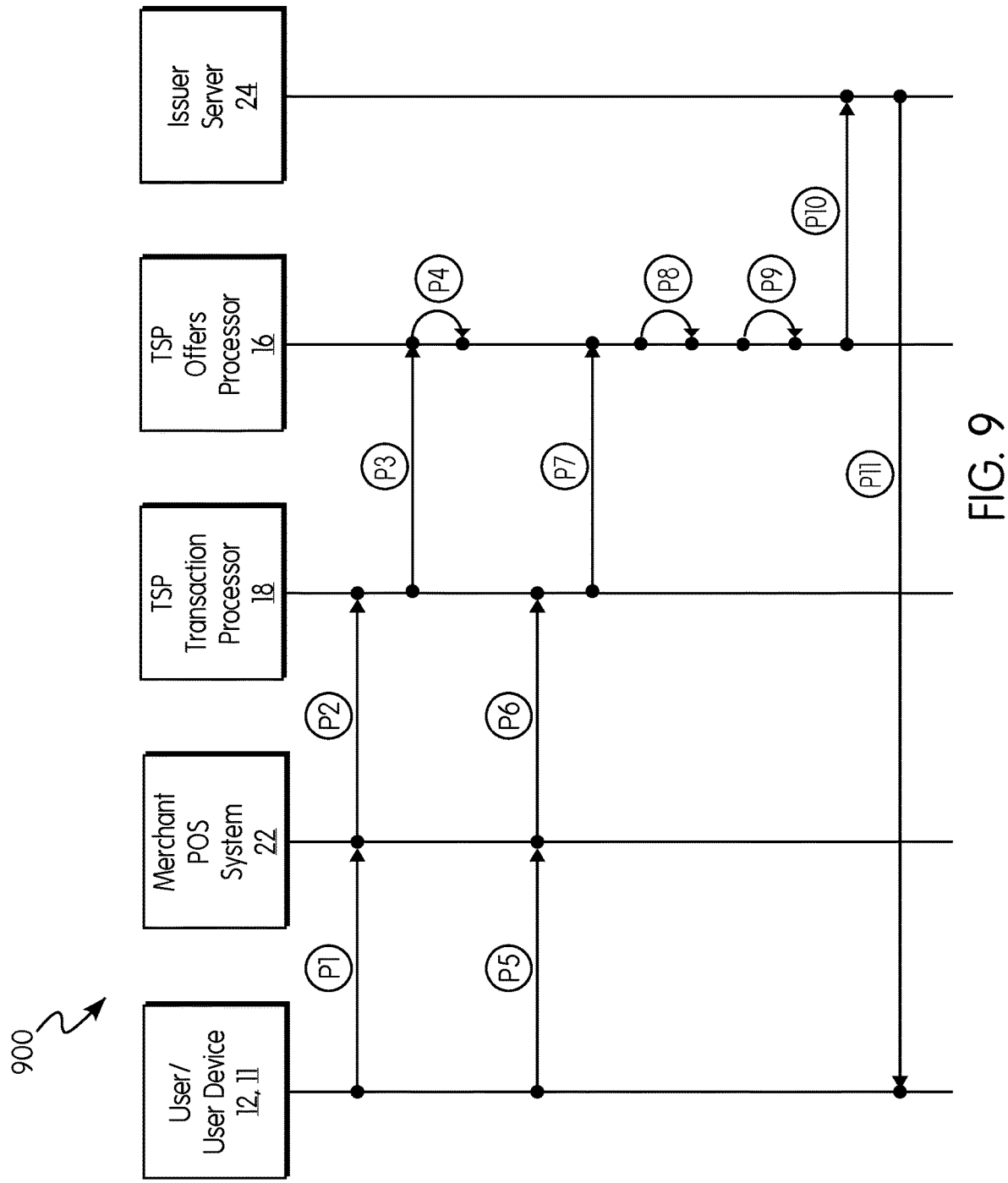
FIG. 9 is a process flow diagram of one non-limiting embodiment or aspect of a method for tracking and incentivizing wellness activity according to principles of the present invention.

Referring to FIGS. 7-9, a process flow diagrams of non-limiting methods 700, 800, 900 for tracking and incentivizing wellness activity are shown.

Referring to FIG. 7, User A (e.g., a user 12) is a cardholder of a portable financial device (e.g., a credit card) managed by First Credit Card Company (e.g., a transaction service provider) and issued by First Issuer Bank (e.g., an issuer). First Issuer Bank may have a First Issuer Bank Server. User A uses the portable financial device to initiate transactions with various merchant point-of-sale systems 22, such as a merchant point-of-sale system of Merchant A and Merchant B, which accept the portable financial device as a form of payment. User A also uses a fitness tracking device 10 to track his/her daily physical activity, the fitness tracking device 10 having the capability of collecting wellness data including wellness metrics 14. First Issuer Bank sponsors an offers program entitled "Reward Program" including a "Step Program", facilitated by First Credit Card Company, for holders of the portable financial device used by User A. In the Step Program, the user receives a wellness award for a time period based at least partially the user's performance of wellness activity (e.g., wellness metric or other wellness activity) over the time period and the user's spending over the time period. In this example, all users, including User A, are automatically enrolled in Step Program by being a holder of the portable financial device. Step Program includes a system-generated wellness goal 30 of a certain number of daily steps for User A each day, and provides User A a wellness award for his/her daily spending that day based on the number of steps. Step Program includes the rewards structure 26 shown in FIG. 3, such that the wellness award is a percent cash back for all purchases made that day based on the total step count for the day. The day length may be the same for each user. In this example, however, the day length for User A is based on user wellness data from User A's fitness tracking device 10 (e.g., based on the data collected associated with the sleep pattern of User A for that day).

With continued reference to FIG. 7, at a first step (s1), User A initiates transactions during Day 1 (the time period) with various merchant point-of-sale systems 22, for example, of Merchant A, Merchant B, etc. The transactions between User A and the merchant point-of-sale systems 22 may be a purchase of a good and/or service initiated using User A's portable financial device. During Day 1, User A spends a certain amount of money (Total 1) at the various merchant point-of-sale systems 22 using the portable financial device. At a second step (s2), the various merchant point-of-sale systems 22 communicate User A's transaction data with First Credit Card Company (e.g., the transaction processor 18 of First Credit Card Company) to further process the transactions made by User A with the portable financial device during Day 1.

With continued reference to FIG. 7, at a third step (s3), First Credit Card Company (e.g., the offers processor 16 of First Credit Card Company) receives user wellness data from the fitness tracking device 10 of User A. The user wellness data may be received by the offers processor 16 from the fitness tracking device 10. The user wellness data may include the wellness metric 14 of the step count of User A for Day 1. The user wellness data may be received by the offers processor 16 from the fitness tracking device 10 of User A after User A's day has ended (e.g., after the fitness tracking device 10 determines that User A has gone to sleep for the day). Thus, the offers processor 16 may receive how many steps User A has taken on Day 1.

With continued reference to FIG. 7, at a fourth step (s4), the offers processor 16 may receive transaction data of User A for Day 1 from the transaction processor 18. The offers processor 16 may automatically receive the transaction data for Day 1 from the transaction processor 18 or request the transaction data for Day 1 from the transaction processor 18. In some non-limiting embodiments or aspects, the offers processor 16 and the transaction processor 18 may be the same processor. At a fifth step (s5), the offers processor 16 analyzes the user transaction data of User A for Day 1. The transaction data of User A for Day 1 may be analyzed to determine Total 1. The transaction data for User A for Day 1 may be received by the offers processor 16 from the transaction processor 18 after User A's day has ended (e.g., after the fitness tracking device 10 determines that User A has gone to sleep for the day). Thus, the offers processor 16 may receive Total 1 for User A for Day 1.

With continued reference to FIG. 7, at a sixth step (s6), the offers processor 16 automatically determines a wellness award for Day 1 for User A. The award for Day 1 may be based at least partially on the number of steps by User A on Day 1 and Total 1. The wellness award for the Step Program is determined using the rewards structure 26 from FIG. 3. From this rewards structure 26, the percent cash back for User A on Day 1 is determined based on the number of steps. For example, if the total number of steps by User A on Day 1 is 12,345, the percent cash back for User A would be 2% (see FIG. 3). Thus, the wellness award (WA) for User A for Day 1 would be calculated according to the following formula: WA=(0.02)(Total 1). For example, if User A spent $100 total on Day 1, the wellness award would be $2.00.

With continued reference to FIG. 7, at a seventh step (s7), the offers processor 16 communicates the wellness award to First Issuer Bank Server. In some non-limiting embodiments or aspects, the offers processor 16 may only communicate raw data associated with User A (e.g., Total 1 and steps by User A) to First Issuer Bank Server, and it is First Issuer Bank Server that analyzes the data to determine the wellness award for User A. At an eighth step (s8), the First Issuer Bank Server applies the wellness award for User A to an account of User A. This may include providing a statement credit or otherwise communicating the wellness award to User A. In some non-limiting embodiments or aspects, First Credit Card Company (e.g., the offers processor 16) may instead apply the wellness award to the account of User A or otherwise communicate the wellness award to User A. For example, User A may have an account balance of ($100.00) at the end of Day 1 before applying the wellness award; however, after Day 1, the $2.00 wellness award may be credited to the account of User A such that the account balance at the end of Day 1 is ($98.00). Wellness awards other than statement credit are contemplated.

Referring to FIG. 8, the method 800 includes all of the features and functions of the method 700 in FIG. 7 having the same reference numbers. The method 800 of FIG. 8 may differ from the method 700 of FIG. 7 in that User A may not automatically be enrolled in the Step Program portion of Reward Program or may be enrolled in another program ("Goal Program") of Reward Program in addition to Step Program. At a step 0 (s0), User A (via a smartphone of User A (a user device 11 of User A)) and the offers processor 16 communicate regarding the Goal Program to enroll User A in the Goal Program. The Goal Program provides User A with a wellness award for successfully completing a goal over the time period. In some non-limiting embodiments or aspects, the goal of Goal Program is a user-generated wellness goal 28, as previously described, and FIG. 4A shows exemplary user-generated wellness goals 28. For Example, User A's user device 11 may communicate a user-generated wellness goal 28 of completing a 5k race in May, which is subsequently approved. In some non-limiting embodiments or aspects, the goal of Goal Program is a system-generated wellness goal 30, as previously described, and FIG. 4B shows exemplary system-generated wellness goals 30. For Example, User A may accept at least the system-generated wellness goal 30 of completing a marathon in the next six months. The remaining steps of the method 800 in FIG. 8 are identical to those of method 700 in FIG. 7, such that User A is provided with a wellness award for successful completion of the accepted goal of the Goal Program.

Referring to FIG. 9, User B (e.g., a user 12) is a cardholder of a portable financial device (e.g., a credit card) managed by Second Credit Card Company (e.g., a transaction service provider) and issued by Second Issuer Bank (e.g., an issuer). The Second Issuer Bank has a Second Issuer Bank Server. User B uses the portable financial device to initiate transactions with various merchant point-of-sale systems 22, such as merchant point-of-sale systems 22 of Merchant C and Merchant D, which accept the portable financial device as a form of payment. Second Issuer Bank sponsors an offers program entitled "Wellness Program", facilitated by Second Credit Card Company, for holders of the portable financial device used by User B. In Wellness Program, the user receives a wellness award for a time period based at least partially the user's performance of a wellness activity over the time period and the user's spending over the time period.

With continued reference to FIG. 9, at a first step (p1), before the time period, User B initiates transactions with various merchant point-of-sale systems 22, for instance, of Merchant C, Merchant D, etc. The transactions between User B and the merchant point-of-sale systems 22 may be exchanges of goods and services for some monetary value, and the transactions are initiated using User B's portable financial device. At a second step (p2), before the time period, the various merchant point-of-sale systems 22 communicate with Second Credit Card Company (e.g., the transaction processor 18 of Second Credit Card Company) to further process the transactions made by User B before the time period. The data transmitted from the merchant point-of-sale systems 22 to transaction processor 18 of the transactions made by User B is considered historical transaction data since the data relates to transactions initiated before the time period. At a third step (p3), before the time period, the transaction processor 18 communicates the historical transaction data to the offers processor 16 of Second Credit Card Company. In some non-limiting embodiments or aspects, the offers processor 16 and the transaction processor 18 are the same processor.

With continued reference to FIG. 9, at a fourth step (p4), the offers processor 16 analyzes the historical transaction data for User B and generates and communicates to User B's user device a suggested user wellness activity to be completed over a time period (e.g., the system-generated wellness goal 30) by User B, which, if successfully completed, yields a wellness award for User B. The suggested user wellness activity may be based at least partially on the historical user transaction data for User B. FIG. 4B shows non-limiting examples of suggested user wellness activities for User B. User B may accept or reject any of the suggested user wellness activities with the user device 11 and communicate that acceptance or rejection to the offers processor 16. In this Example, User B accepts the suggested user wellness activity in the eighth row of FIG. 4B of spending $250 or more on organic food in May. Thus, for this goal, the time period is one month (May) and the wellness award is a 2.5% cash back for all purchases made with the portable financial device in May.

With continued reference to FIG. 9, at a fifth step (p5), User B initiates transactions in May with the various merchant point-of-sale systems 22, for instance, of Merchant C, Merchant D, etc. The transactions between User B and the merchant point-of-sale systems 22 may be exchanges of goods and services (given to User B) for some monetary value (given to the merchant point-of-sale systems 22), and the transactions are initiated using User B's portable financial device. In May, User B spends a certain amount of money (Total 2) at various merchant point-of-sale systems 22 using the portable financial device. At a sixth step (p6), the various merchant point-of-sale systems 22 communicate with Second Credit Card Company (e.g., the transaction processor 18 of Second Credit Card Company) to further process the transactions made by User B with the portable financial device in May. At a seventh step (p7), the offers processor 16 may receive transaction data of User B for May from the transaction processor 18. The offers processor 16 may receive the transaction data for User B for May from the transaction processor 18 or receive that transaction data for May from the transaction processor 18.

With continued reference to FIG. 9, at an eighth step (p8), the offers processor 16 analyzes the user transaction data of User B for May. The transaction data of User B for May may be analyzed to determine Total 2. The transaction data for User B for May may be received by the offers processor 16 from the transaction processor 18 after May has ended. Thus, the offers processor 16 may receive Total 2 for User B for May.

At a ninth step (p9), the offers processor 16 automatically determines a wellness award for May for User B if User B completes the accepted suggested user wellness activity (spending at least $250 on organic food). Thus, the wellness award for May may be based at least partially on User B successfully buying at least $250 in organic food and Total 2. For example, if User B spent $250 in organic food in May with the portable financial device, the percent cash back for User B would be 2.5% (see FIG. 4B) for all purchases made in May with the portable financial device (Total B). Thus, the wellness award for User B for May would be calculated according to the following formula: WA=(0.025)(Total 2). For example, if User B spent $1,000 using the portable financial device in May, the wellness award would be $25.00.

With continued reference to FIG. 9, at a tenth step (p10), the offers processor 16 communicates the wellness award to Second Issuer Bank Server. In some non-limiting embodiments or aspects, the offers processor 16 may only communicate raw data associated with User B (e.g., Total 2 and transaction data for May of User B) to Second Issuer Bank Server, and it is Second Issuer Bank Server that analyzes the data to determine the wellness award for User B. At an eleventh step (p11), Second Issuer Bank Server applies the wellness award for User B to an account of User B. This may include providing a statement credit or otherwise communicating the wellness award to User B. In some non-limiting embodiments or aspects, Second Credit Card Company (e.g., the offers processor 16) may instead apply the wellness award to the account of user B or otherwise communicate the wellness award to User B. For example, User B may have an account balance of ($100.00) at the end of May before any wellness award is determined; however, after the May wellness award of $25.00 is determined, the wellness award may be credited to the account of User B such that the account balance at the end of May is ($75.00).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for tracking and incentivizing wellness activity using a fitness tracking device, comprising:
   receiving, with a first processor of a transaction processing system of a transaction service provider configured to execute functions of an offers program facilitated by the transaction service provider, a value associated with a wellness metric received from at least one fitness tracking device of a user;
   determining, with the first processor, the value associated with the wellness metric;
   receiving, with a second processor of the transaction processing system and from a first merchant system of a first merchant, first user transaction data associated with a first transaction between the user and the first merchant initiated with a portable financial device of the user, the second processor configured to execute functions for processing payment transactions initiated by portable financial devices;
   receiving, with the second processor and from a second merchant system of a second merchant, second user transaction data associated with a second transaction between the user and the second merchant initiated with the portable financial device;
   receiving, with the first processor and from the second processor, the first user transaction data and the second user transaction data;
   based on the first user transaction data and the second user transaction data, determining, with the first processor, a total transaction spend amount for the user;
   based on the value associated with the wellness metric and the total transaction spend amount for the user, determining, with the first processor, a wellness award amount;
   generating, with the first processor, a message comprising the wellness award amount; and
   causing, with the first processor, an issuer server operated by or on behalf of an issuer of an account of the user associated with the portable financial device to apply the wellness award amount to the account of the user by communicating the message to the issuer server.

2. The method of claim 1, wherein the wellness metric comprises at least one of the following: steps taken, calories burned, weight lost, distance travelled, calories consumed, fluids consumed, floors climbed, time active, heart rate, sleep duration, or any combination thereof.

3. The method of claim 1, wherein the wellness metric comprises a user wellness goal generated by the user, wherein the wellness award amount is automatically applied to the account of the user in response to completion of the user wellness goal.

4. The method of claim 1, wherein the wellness metric comprises a suggested wellness goal generated by the first processor.

5. The method of claim 4, wherein the suggested wellness goal is generated based at least partially on historical user wellness data.

6. The method of claim 4, wherein the suggested wellness goal is generated based at least partially on historical user transaction data.

7. The method of claim 1, wherein the wellness award amount comprises a statement credit applied to the account of the user.

8. The method of claim 1, wherein the at least one fitness tracking device comprises at least one of the following: a wearable fitness device, a smartphone, a smartwatch, a heartrate monitor, a pedometer, a global positioning system (GPS), or any combination thereof.

9. A system for tracking and incentivizing wellness activity using a fitness tracking device, comprising a transaction processing system of a transaction service provider comprising a first processor and a second processor, the first processor configured to execute functions of an offers program facilitated by the transaction service provider, and the second processor configured to execute functions for processing payment transactions initiated by portable financial devices, the transaction processing system programmed and/or configured to:
   receive, with the first processor, a value associated with a wellness metric received from at least one fitness tracking device of a user,
   determine, with the first processor, the value associated with the wellness metric;
   receive, with the second processor and from a first merchant system of a first merchant, first user transaction data associated with a first transaction between the user and the first merchant initiated with a portable financial device of the user, the second processor configured to execute functions for processing payment transactions initiated by the portable financial devices;
   receive, with the second processor and from a second merchant system of a second merchant, second user transaction data associated with a second transaction between the user and the second merchant initiated with the portable financial device;
   receive, with the first processor and from the second processor, the first user transaction data and the second user transaction data;
   based on the first user transaction data and the second user transaction data, determine, with the first processor, a total transaction spend amount for the user;
   based on the value associated with the wellness metric and the total transaction spend amount for the user, determine, with the first processor, a wellness award amount;
   generate, with the first processor, a message comprising the wellness award amount; and
   cause, with the first processor, an issuer server operated by or on behalf of an issuer of an account of the user associated with the portable financial device to apply the wellness award amount to the account of the user by communicating the message to the issuer server.

10. The system of claim 9, wherein the wellness metric comprises at least one of the following: steps taken, calories burned, weight lost, distance travelled, calories consumed, fluids consumed, floors climbed, time active, heart rate, sleep duration, or any combination thereof.

11. The system of claim 9, wherein the wellness metric comprises a user wellness goal generated by the user, wherein the wellness award amount is automatically applied to the account of the user in response to completion of the user wellness goal.

12. The system of claim 9, wherein the wellness metric comprises a suggested wellness goal generated by the first processor.

13. The system of claim 12, wherein the suggested wellness goal is generated based at least partially on historical user wellness data.

14. The system of claim 12, wherein the suggested wellness goal is generated based at least partially on historical user transaction data.

15. The system of claim 9, wherein the wellness award amount comprises a statement credit applied to the account of the user.

16. The system of claim 9, wherein the at least one fitness tracking device comprises at least one of the following: a wearable fitness device, a smartphone, a smartwatch, a heartrate monitor, a pedometer, a global positioning system (GPS), or any combination thereof.

17. A method for tracking and incentivizing wellness activity using a fitness tracking device, comprising:
   receiving, with a first processor of a transaction processing system of a transaction service provider, historical user transaction data associated with at least one payment transaction initiated by at least one portable financial device of a user between the user and at least one merchant, wherein the historical user transaction data is received from at least one merchant system, the first processor configured to execute functions for processing payment transactions initiated by portable financial devices;
   receiving, with a second processor of the transaction processing system and from the first processor, the historical user transaction data, wherein the second processor is configured to execute functions of an offers program facilitated by the transaction service provider;
   applying, with the second processor, a machine-learning algorithm to the historical user transaction data to generate a suggested user wellness activity;
   monitoring, with the second processor, user activity by receiving user wellness data associated with at least one wellness metric from at least one fitness tracking device of the user;
   based on the received user wellness data, determining, with the second processor, completion of the suggested user wellness activity by the user;
   in response to the user completing the suggested user wellness activity, determining, with the second processor, a wellness award amount;
   generating, with the second processor, a message comprising the wellness award amount; and
   causing, with the second processor, an issuer server operated by or on behalf of an issuer of an account of the user associated with the portable financial device to apply the wellness award amount to the account of the user by communicating the message to the issuer server.

18. The method of claim 17, wherein the wellness metric comprises at least one of the following: steps taken, calories burned, weight lost, distance travelled, calories consumed, fluids consumed, floors climbed, time active, heart rate, sleep duration, or any combination thereof.

19. The method of claim 17, wherein the wellness award amount comprises a statement credit applied to the account of the user.

20. The method of claim 17, wherein the at least one fitness tracking device comprises at least one of the following: a wearable fitness device, a smartphone, a smartwatch, a heartrate monitor, a pedometer, a global positioning system (GPS), or any combination thereof.

* * * * *